United States Patent [19]

Dawn et al.

[11] 4,338,371
[45] Jul. 6, 1982

[54] ABSORBENT PRODUCT TO ABSORB FLUIDS

[75] Inventors: Frederic S. Dawn, Houston; James V. Correale, Seabrook, both of N.Y.

[73] Assignee: The United States of America as represented by the Administrator of the National Aeronautics and Space Administration, Washington, D.C.

[21] Appl. No.: 219,681

[22] Filed: Dec. 24, 1980

[51] Int. Cl.$^3$ ............................................. A61F 13/16
[52] U.S. Cl. .................................... 428/283; 128/280; 128/283; 128/284; 128/285; 128/288; 128/291; 128/296; 428/284; 428/286; 428/287; 428/288
[58] Field of Search ............... 128/280, 283, 284, 285, 128/287, 288, 290 R, 290 W, 291, 296; 428/283, 284, 286, 287, 288

[56] References Cited

U.S. PATENT DOCUMENTS 4,044,769  8/1977  Papajohn ............................ 128/288

*Primary Examiner*—Marion McCamish
*Attorney, Agent, or Firm*—Edward K. Fein; John R. Manning; Marvin F. Matthews

[57] ABSTRACT

A multi-layer absorbent product (10) for use in contact with the skin to absorb fluids, the product having a water pervious facing layer (12) for contacting the skin, a first fibrous wicking layer (14) overlaying the water pervious layer, a first container section (17) defined by inner and outer layers (16, 18) of a water pervious wicking material between which is disposed a first absorbent mass (20), a second container section (26) defined by inner and outer layers (22, 24) of a water pervious wicking material between what is disposed a second absorbent mass (28), and a liquid impermeable/gas permeable layer (30) overlaying the second fibrous wicking layer.

12 Claims, 3 Drawing Figures

ABSORBENT PRODUCT TO ABSORB FLUIDS

ORIGIN OF THE INVENTION

The invention described herein was made by employees of the U.S. Government and may be manufactured and used by or for the Government of the United States of America for governmental purposes without the payment of any royalties thereon or therefor.

BACKGROUND OF THE INVENTION

1. Field of the Invention

The present invention relates to absorbent products and articles of manufacture made therefrom. More particularly, the present invention relates to an absorbent product suitable for use in a disposable collection device for body waste products such as urine and fecal matter.

During extravehicular activity (EVA) by astronauts in space flight operations, it is desirable that there be a body waste collection device which may be worn inside the space suit of the astronaut and which will collect and retain at least about 900 cc of urine and fecal matter while imposing minimal discomfort to the wearer. In order to be effective, any such collection device must be leakproof even when the wearer thereof undergoes extreme body movements such as might be encountered in EVA. While collection devices in which the body wastes are collected as it is dispelled from the body and transferred to a collection vessel may be employed, such devices are generally difficult and expensive to manufacture. Moreover, such devices must be made with great care to ensure that they are leakproof.

In addition to body waste matter collecting device for use by astronauts, there are numerous other instances where it is desirable, and indeed even necessary, that there be some sort of device or fluid absorbent product which can be utilized to absorb or in some other fashion remove from the skin surface certain bodily fluids. Typical examples are baby diapers, female hygiene napkins, hospital bed pads, urine collection devices in applications where use of commodes is not feasible such as terminally ill patients, race car drivers, fighter plane pilots, etc.

2. Prior Art

U.S. Pat. No. 4,055,180 to Karami discloses an absorbent article comprising various absorbent and wicking layers and a hydrocolloid material to absorb the fluid and keep it away from the body of the user. U.S. Pat. No. 4,055,184 to Karami discloses an absorbent pad comprising a fluid impervious backing layer, a fluid pervious facing layer, and an intermediate layer of an absorbent hydrocolloid material consisting of hydrolyzed starch-polyacrylonitrile copolymer in the acidic state combined with a basic substance. U.S. Pat. No. 3,903,889 to Torr discloses a multi-layer absorbent material incorporating an absorbent bent hydrocolloid, while U.S. Pat. No. 4,044,769 to Papajohn discloses an undergarment such as a panty or the like incorporating an absorptive portion. None of the art discussed above teaches an absorbent product suitable for use in a body waste matter collection device for a user undergoing marked physical activity.

SUMMARY OF THE INVENTION

It is therefore an object of the present invention to provide a multi-layer, absorbent product for use in devices and articles for absorbing and retaining fluids.

Another object of the present invention is to provide an absorbent product for use in body waste matter collecting devices or articles which can be incorporated into undergarments and the like.

Still a further object of the present invention is to provide a multi-layer absorbent product which utilizes a gel forming absorbent mass to absorb and retain the liquid and hence prevent its migration once it has been absorbed.

The above and other objects of the present invention will become apparent from the drawings, the description given herein and the appended claims.

In one embodiment, the present invention provides a multilayer, absorbent product for use in contact with the skin, e.g. as in a sanitary napkin, a diaper, etc. The absorbent product utilizes a water pervious facing layer for contacting the skin, overlayed by a first fibrous wicking layer, the wicking layer preferably being of the one-way variety in which the fluid or liquid is moved away from the facing layer. The product further includes a first container section having an inner layer and an outer layer which define a first absorbent container therebetween, the inner layer of the first container section being contiguous the first fibrous wicking layer. The first container section is comprised of a water pervious, wicking material which freely permits the ingress and/or egress of liquids. Disposed in the first absorbent container is a first absorbent mass which may be in the form of a film, powder, or other particulate form, and which can be dispersed, suspended or otherwise contained in a matrix of a foamed or fibrous woven or non-woven material to prevent its migration. The first absorbent mass comprises a super absorbent, high-molecular weight acrylic polymer containing hydrophilic carboxylate groups and which forms a gel upon contact with an aqueous medium such as urine. The absorbent product further includes a second container section having an inner layer and an outer layer which defines a second absorbent container, the inner layer of a second container section being contiguous of the outer layer of the first container section. The second container section is also comprised of a water pervious material which freely permits the ingress and/or egress of liquids. Disposed in the second absorbent container is a second absorbent mass which may be in a form the same or similar to the first absorbent mass and which is comprised of a hydrolyzed starch-polyacrylonitrile graft copolymer and which, like the first absorbent mass, forms a gel upon contact with an aqueous medium such as urine. Contiguous the outer layer of the second container section is a liquid impermeable, gas permeable layer, i.e. a backing layer.

In another embodiment, the present invention provides an undergarment such as a panty or the like, the undergarment having a front, rear and opposite sides cooperating to define a lower torso garment with a waist opening and right and left leg openings. The inner core of the undergarment is comprised of the multi-layer absorbent product described above and extends generally throughout the undergarment. An outer covering encapsulates the inner core and is generally made of a stretch spandex fabric adapted to conform to the shape of the body of the wearer of the undergarment.

DESCRIPTION OF THE PREFERRED EMBODIMENTS

The absorbent product of the present invention, as indicated above, is useful in the construction of disposable type liquid absorbent articles including disposable diapers, bed pads, and catamenial devices, and finds particular application in the construction of urine and fecal collection devices, as will be described hereafter.

Figure 1:
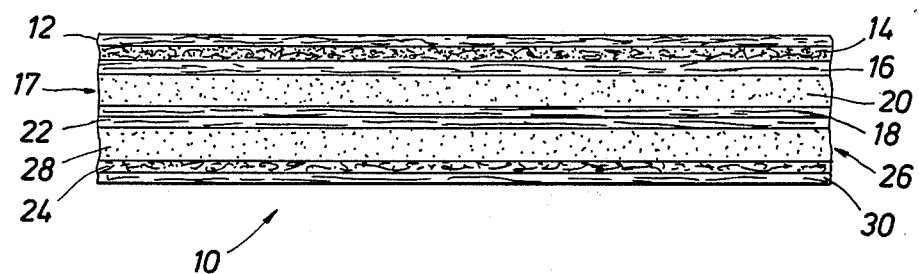
FIG. 1 is an elevational, sectional view of an absorbent product made in accordance with the present invention.

Referring first to FIG. 1, the absorbent product, shown generally at 10, is multi-ply in nature and comprises a facing layer 12, facing layer 12 being water pervious and being the layer which contacts the skin when the absorbent product is made into an undergarment or the like. Facing layer 12 serves the purposes of providing body comfort, retains the succeeding layers of the absorbent products and permits the free flow of urine or other liquid to the other layers of the absorbent product 10. Generally speaking, facing layer 12 can be made of virtually any fabric provided it is water pervious to allow free flow of urine or other liquid therethrough. Thus, for example, layer 12 can be made of cotton, nylon, polyester, cotton-polyester blends or numerous other natural, synthetic or mixed fabrics. Preferably, facing layer 12 is a sheer wicking fabric which tends to facilitate the movement of urine or other liquids away from the skin.

Contiguous facing layer 12 is a first fibrous, wicking layer 14, preferably in the form of a sheer web comprised of a non-woven cellulosic material such as a batting of cotton, fibrous synthetic material, or the like. Wicking layer 14, like layer 12, is preferably a one-way wicking material which tends to move liquids in a direction away from facing layer 12. Contiguous fiber wicking layer 14 is the inner layer 16 of a first container section of the absorbent product, inner layer 16 being formed of a sheer web of a non-woven cellulosic or fibrous synthetic material which is highly water permeable or pervious. The first container section is further comprised of an outer layer 18 whose material of construction may be the same as layer 16. Layers 16 and 18 combine to form an absorbent container 17 therebetween. It will be apparent that layers 16 and 18, depending upon the shape of the absorbent product, can be bonded together at their peripheries so as if to form a pouch or the like defining the absorbent container 17.

Disposed in the absorbent container 17, i.e. between layers 16 and 18 is a highly absorbent mass 20 which possesses the property of forming a gel when contacted with urine or some other aqueous medium thereby essentially preventing migration of the urine.

The absorbent mass 20 comprises a product formed from a high molecular weight acrylic polymer containing hydrophilic carboxylate groups and crosslinked in a manner which ensures high insolubility and rapid swellability in aqueous fluids, e.g. urine. Such polymers and methods of preparation are disclosed in U.S. Pat. No. 3,425,971, incorporated herein by reference for all purposes.

Contiguous outer layer 18 is the inner layer 22 of the second container section of the absorbent product 10, inner layer 22 being formed of a sheer web of a non-woven cellulosic or fibrous synthetic material which is highly water permeable or pervious. The second container section is further comprised of an outer layer 24 whose material of construction is desirably the same as that of the first fibrous wicking layers 14. As in the case of the first container section, layers 22 and 24, depending upon the shape of the absorbent product 10, can be bonded together at their peripheries so as to form a pouch or the like defining a second absorbent chamber 26. Disposed in the absorbent container 26, i.e. between layers 22 and 24, is a highly absorbent mass 28 which, like absorbent mass 20, possesses the property of forming a gel when contacted with urine or some other aqueous medium thereby essentially preventing migration of the urine. The absorbent mass 28 is preferably comprised of a product formed from a graft copolymer of acrylonitrile and starch. The starch acrylonitrile copolymers and methods of preparation are described in U.S. Pat. No. 3,997,484, incorporated herein by reference for all purposes.

To obtain the desired absorbent mass 28, acrylonitrile is reacted with equal weight amounts of a suitable starch product in an aqueous medium in the presence of cerric ammonium nitrate. The starch-polyacrylonitrile graft copolymer is then treated with hot alkali followed by saponification to produce a graft copolymer containing alkali metal carboxylate and carboxamide constituents. The saponified copolymer is then isolated, dried and formed into the desired physical form. The hydrolyzed starch-polyacrylonitrile graft polymer, following saponification, reacts with urine or such other aqueous medium to form a gel thereby substantially immobilizing the urine thereby containing it.

It will be appreciated that, depending upon the degree of absorbency required, the amount of the absorbent masses 20 and 28 employed can vary widely. For example in the construction of a urine collecting device in the form of a disposable undergarment to be worn by astronauts it is generally necessary that the degree of absorbency be such as to contain or retain at least 900 cc of fluid. The gel which forms by reaction of the aqueous medium, e.g. urine and the absorbent masses 20 and 28 will not discharge its liquid even under compressive loading. Since the urine is immobilized in a firm gel, the surface layers of the garment dry rapidly thereby preventing chaffing or irritation to the skin of the wearer. The absorbent masses 20 and 28, can be in the form of films, powders or other particulate forms, or impregnated in fibrous material form, can be admixed with materials such as talc, diamataceous earth or other generally inert filler ingredients if desired. In FIG. 1 the absorbent masses 20 and 28 are depicted in a particulate form, the particulate masses being prevented from migration by their encapsulation in the first and second container sections formed by first container layers 16 and 18 and second container layers 22 and 24, respectively.

It further will be appreciated that the polymer absorbent mass 20 gels slower and absorbs more fluid than does the copolymer mass 28. The copolymer mass 28 gels faster such as to effect rapid blocking of the fluid flow and prevent leakage. It is this relationship between absorbent masses 20 and 28 which permit a redundant capability of leakage avoidance such that in case of oversaturation of the polymer, the fluid will absorb into the copolymer mass, which will rapidly gel, thus blocking further fluid flow.

Contiguous the outer fibrous wicking layer 24 of the second container section is a liquid impermeable/gas permeable backing layer 30 which serves the purpose of trapping the liquid within the absorbent product 10. Backing layer 30, along with containing the liquids until gelation has occurred, also provides a breathable function to the absorbent product 10. Suitable materials which can be utilized in forming the backing layer include various synthetic fibers, coated woven synthetic fabrics and the like, the requisite being that the backing layer retain the liquids within the absorbent product until reaction between the liquid and the absorbent masses to form the gel has occurred.

Figure 2:
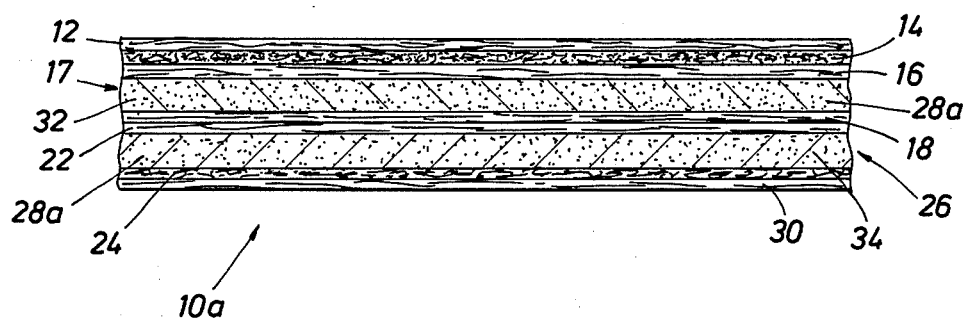
FIG. 2 is a view similar to FIG. 1 showing a slightly different embodiment of an absorbent product made in accordance with the present invention.

In FIG. 2 there is shown a slightly modified embodiment of the absorbent product shown in FIG. 1. Absorbent product 10a shown in FIG. 2 is modified to the extent that the absorbent masses 20a and 28a are comprised of the polymer and copolymer, respectively, and described above disposed in water pervious matrices 32 and 34, respectively. The water pervious matrices may be in the form of foamed materials, fibrous materials, or woven or non-woven materials. The use of such matrices prevents migration of the absorbent masses thereby ensuring uniform distribution of the surface absorbent masses e.g. the polymer 20 and copolymer 28 through the absorbent product 10a. It will be appreciated that the matrix materials must be water permeable to ensure that rapid contact between the liquid and the absorbent masses can occur. The matrix materials may be comprised, with advantage of wicking type materials.

Figure 3:
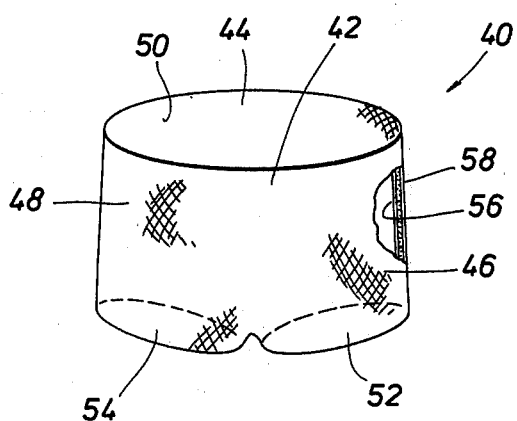
FIG. 3 is an isometric view, with a portion cut away, showing an undergarment embodying the absorbent product of the present invention.

Referring now to FIG. 3, there is shown an undergarment employing the absorbent product of the present invention. The undergarment 40 has a front section 42, back section 44 and side sections 46 and 48 which together cooperatively define a waist opening 50 and left and right leg openings 52 and 54, respectively. The undergarment 40 has an inner core 56 comprised of an absorbent product such as shown in either FIG. 1 or 2. Inner core 56 extends for substantially the full extent of undergarment 40, i.e. it is generally in the form of the undergarment 40. Covering the outer surface of inner core 46 is an outer covering 58 comprised of a stretch spandex fabric adapted to conform to the shape of the body of the wearer of undergarment 40. Thus, the facing material 11 layer 12 is in contact with the body. The stretch fabric can be, for example, made of spandex or other elastic fibrous material. It will be appreciated that outer covering 58, like inner core 56, is substantially in the form of undergarment 40. Methods of constructing undergarments such as undergarment 40 are well known to those skilled in the art and need not be discussed in detail here.

A female undergarment was made in accordance with the teachings of the present invention. The outer coverings of the undergarment was made of Spandex. The facing layer, i.e. layer 12, was made of a fine denier filament nylon which formed a sheer fabric. A non-woven, one-way wicking layer, i.e. layer 14 was contiguous the facing layer. The first absorbent container was made from non-woven cellulosic material and contained, as an absorbent bent mass, a high molecular weight super absorbent acrylic polymer, in granular form, and made in accordance with U.S. Pat. No. 3,425,971. The second absorbent container was made from absorbent wadding cellulose and was filled with a graft copolymer of acrylonitrile and starch made in accordance with U.S. Pat. No. 3,997,484.

The liquid impermeable/gas permeable layer contiguous Spandex outer layer was made of a polyolefinic material. The garment thus produced had a weight of 368 grams. In an actual test of the garment by a female subject, 74 tc's of urine was expanded. The garment was found to be very satisfactory in terms of minimal discomfort to the subject, particularly as to a feeling of dampness against the body. Only minor wicking of fluid through the seam threads was observed.

It will be understood that the various configurations and the materials of construction of the absorbent product disclosed herein are virtually endless. Accordingly, the configurations and materials of construction depicted and discussed above are merely illustrative and are not intended in any way to limit the scope of the invention either with regard as to the type of absorbent material or to the type of construction employed.

We claim:

1. A multi-layer, absorbent product for use in contact with the skin comprising:
   a. a water pervious facing layer for contacting the skin;
   b. a first fibrous, wicking layer contiguous said water pervious layer;
   c. a first container section having an inner layer and an outer layer forming a first absorbent container therebetween, said container section being comprised of a water pervious material, said inner layer being contiguous said first fibrous, wicking layer;
   d. a first absorbent mass disposed in said first absorbent container, said first absorbent mass comprising a super absorbent high molecular weight acrylic polymer containing hydrophilic carboxylate groups said polymer forming a gel upon contact with an aqueous medium;
   e. a second container section having an inner layer and said outer layer container therebetween, said second container section being comprised of a water pervious material, said inner layer of said second container being contiguous said outer layer of said first container section;
   f. a second absorbent mass disposed in said second absorbent container, said second absorbent mass comprising a hydrolyzed starch-acrylonitrile graft copolymer, said copolymer forming a gel upon content with an aqueous medium; and
   g. a liquid impermeable/gas permeable layer contiguous said outer layer of said second container section.

2. The product of claim 1 wherein said water pervious facing layer comprises a sheer wicking fabric.

3. The product of claim 1 wherein said first fibrous, wicking layer is selected from the class consisting of non-woven cellulosic batting material, synthetic batting material and mixtures thereof.

4. The product of claim 1 wherein said first container section comprises a sheer web of material selected from the class consisting of non-woven cellulosic material, non-woven synthetic material, fibrous synthetic material and mixtures thereof.

5. The product of claim 1 wherein said outer layer of said second container section is selected from the class consisting of non-woven cellulosic batting material, synthetic batting material and mixtures thereof.

6. The product of claim 1 wherein said absorbent masses are particulate in nature.

7. The product of claim 1 wherein said absorbent masses are dispersed in a water permeable matrix.

8. The product of claim 7 wherein said matrix comprises a foamed material.

9. The product of claim 7 wherein said matrix is fibrous in nature.

10. The product of claim 1 wherein said first absorbent mass comprises a film of said polymer.

11. The product of claim 1 wherein said second absorbent mass comprises a film of said copolymer.

12. The product of claim 1 wherein said copolymer is formed by reacting acrylonitrile and starch, in equal amounts, in an aqueous medium in the presence of ceric ammonium nitrate.

* * * * *